United States Patent [19]

Khanna et al.

[11] Patent Number: 4,588,697
[45] Date of Patent: May 13, 1986

[54] METHOD FOR PERFORMING FLUORESCENT PROTEIN BINDING ASSAY EMPLOYING NOVEL ALKYL SUBSTITUTED FLUORESCENT COMPOUNDS AND CONJUGATES

[75] Inventors: Pyare Khanna, Mountain View; Edwin F. Ullman, Atherton, both of Calif.

[73] Assignee: Syntex (U.S.A.) Inc., Palo Alto, Calif.

[21] Appl. No.: 664,121

[22] Filed: Oct. 23, 1984

Related U.S. Application Data

[62] Division of Ser. No. 399,506, Jul. 19, 1982, Pat. No. 4,481,136, which is a division of Ser. No. 73,158, Sep. 7, 1979, Pat. No. 4,351,760.

[51] Int. Cl.⁴ ............... G01N 33/543; G01N 33/545; G01N 33/549; G01N 33/533
[52] U.S. Cl. ..................... 436/518; 436/528; 436/531; 436/532; 436/546; 436/800; 436/537; 530/406; 530/307
[58] Field of Search ............... 436/537, 518, 528, 531, 436/532, 546, 800; 260/112 R, 112 B, 121, 112.5 R, 112.7

[56] References Cited

U.S. PATENT DOCUMENTS

| | | | |
|---|---|---|---|
| 4,174,384 | 11/1979 | Ullman et al. | 260/112 R |
| 4,331,590 | 5/1982 | Bocuslaski et al. | 260/112 B |
| 4,351,760 | 9/1982 | Khanna et al. | 260/112 R |
| 4,420,568 | 12/1983 | Wang et al. | 436/546 |
| 4,476,228 | 10/1984 | Huchzermeier et al. | 436/546 |
| 4,476,229 | 10/1984 | Find et al. | 436/546 |
| 4,481,136 | 11/1984 | Khanna et al. | 260/112 B |

Primary Examiner—Christine M. Nucker
Attorney, Agent, or Firm—Carole F. Barrett; Theodore J. Leitereg; Bertram I. Rowland

[57] ABSTRACT

Fluorescent antigen conjugates are provided comprising antigens covalently bonded to at least one 2,7-dialiphatic substituted-9-phenyl-6-hydroxy-3H-xanthen-3-one, wherein the 1- and 8-positions are unsubstituted. Also provided are novel fluorescent compounds absorbing at wavelengths in excess of 500 nm, having active functionalities for linking to the antigen. Finally, methods are provided for analyzing antigens in serum, whereby serum interference is avoided.

5 Claims, No Drawings

METHOD FOR PERFORMING FLUORESCENT PROTEIN BINDING ASSAY EMPLOYING NOVEL ALKYL SUBSTITUTED FLUORESCENT COMPOUNDS AND CONJUGATES

This application is a division of application Ser. No. 399,506, filed July 19, 1982, now U.S. Pat. No. 4,481,136, which is a division of application Ser. No. 73,158, filed Sept. 7, 1979, now U.S. Pat. No. 4,351,760.

BACKGROUND OF THE INVENTION

1. Field of the Invention

Fluorescent compounds find a wide variety of applications. They find use in fluorescent immunoassays, histochemical staining, displays, inks, and the like. Of particular interest for the subject invention is the use of antigenic conjugates (includes receptor conjugates) with fluorescent compounds to be used in the determination of a variety of ligands, both antigens and receptors. A substantial proportion of the ligands are assayed in physiological fluids, such as serum, where the serum can provide substantial background fluorescence. One way to diminish the background fluorescence resulting from naturally present fluorescers is to provide a fluorescent compound which absorbs at relatively long wavelengths. The compound should desirably have a large Stokes shift, be stable under conditions of the assay, be relatively free of non-specific interference, both from materials in solution and the compound to which the fluorescer is conjugated and to provide high quantum yields. In addition, for certain applications, it is desirable that the fluorescer be coupled with a quencher molecule, that is a molecule which is capable of absorbing the energy of the fluorescer in the excited state when within a predetermined distance, so that the fluorescer does not fluoresce.

2. Description of the Prior Art

A large number of fluorescein derivatives have been reported in the literature. The following are believed to be the most exemplary in relation to the subject invention and are reported in conjunction with the Chemical Abstracts citation. The numbering is based on the parent molecule 3',6'-dihydroxyspiro [isobenzofuran-1(3H),9'-(9H)xanthen]-3-one.

2',7'-di(n-hexyl) or di(n-heptyl)-4', 5'-dibromo-4,7-dichloro- are reported as being prepared, C.A. 31, 1621; 2',7'-di(n-hexyl)-, C.A. 31, 1621; 2',7'-di(alkyl)-; C.A. 31, 1388; 2',7'-diethyl or 2',7'-dibutyl-, C.A. 27, 5056; 2',7'-dimethyl-, C.A. 83, 18972s; 2',4',5',7'-tetrabromo-5 or 6-carboxy, C.A. 63, 13210h.

SUMMARY OF THE INVENTION

The subject compounds include novel fluorescent conjugates with members of specific binding pairs, ligands and receptors, as well as the fluorescent precursors to the conjugates. The conjugates find a wide variety of uses, particularly as reagents in immunoassays. The compounds are 2,7-dialiphatic-6-hydroxy-3H-xanthen-3-ones, normally having a least two chloro substituents, with the precursors having a linking group or functionality on a group, either aliphatic or aromatic, bonded to the 2- or 9-position of the xanthene.

DESCRIPTION OF THE SPECIFIC EMBODIMENTS

The subject invention concerns fluorescent compounds, which are analogs of fluorescein, being particularly 2,7-dialiphatic substituted-9-substituted-6-hydroxy-3H-xanthen-3-ones, usually having a least two chloro substituents at other than the 1,8-positions and having a functional group for linking to a member of a specific binding pair bonded to a hydrocarbon group substituted at the 2- or 9-position, particularly 9-position, as well as the conjugates of the fluorescent compound to the member of the specific binding pair. The conjugates find particular use as reagents in assays for members of specific binding pairs.

The fluorescent precursors will have at least about 15 carbon atoms, usually 21 carbon atoms, and usually not more than about 40 carbon atoms, usually having from about 22 to 36 carbon atoms. There will preferably be at least two chlorine groups at other than the 1,8-positions and may be as many as 6 chlorines. In addition to chlorine, the only other heteroatoms are bromine, chalcogen, particularly oxygen and sulfur, and nitrogen, there being at least 4 heteroatoms and usually not more than 20 heteroatoms, more usually not more than about 16 heteroatoms and preferably not more than about 12 heteroatoms. Of the heteroatoms other than chlorine, there will be at least 3 oxygens, more usually at least 5 oxygens, and other than the oxygens which are part of the xanthene chromophore, are oxygens as non-oxo-carbonyl or oxy, particularly acid, ester or ether (normally bonded solely to carbon and hydrogen); sulfur is normally present as sulfonyl, thioether or mercapto; while nitrogen is normally present as amino or amido (bonded solely to carbon and hydrogen).

The fluorescent compounds are further characterized by having absorption maxima in 0.05M phosphate buffer pH8 of at least about 500 nm, an extinction coefficient in the same medium of at least about 65,000, more usually at least 70,000 and a Stokes shift in the same medium of at least about 10 nm, more usually at least about 12 nm.

The 9-substituted-2,7-dialkylsubstituted xanthenes of this invention will for the most part have the following formula:

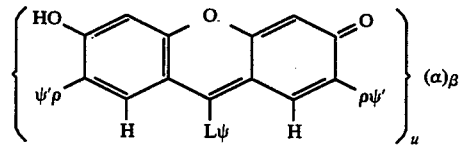

wherein:

ρ is an aliphatic group, normally aliphatic hydrocarbylene (composed solely of carbon and hydrogen), saturated or unsaturated, branched or straight chain, particularly alkylene, more particularly $(CH_2)_\epsilon$, wherein $\epsilon$ is of from 1 to 12, usually 1 to 6, more usually 1 to 4; ρ is normally of from 1 to 12, usually 1 to 6, more usually 1 to 4 carbon atoms;

the two Ψ's are the same or different, normally being the same, except when linking to α, and are hydrogen, a non-oxo-carbonyl functionality or one of the Ψ's may be a non-oxo-carbonyl linking functionality;

L is a bond or divalent radical, usually an organic radical, of at least one carbon atom and not more than 20, usually not more than 16, more usually not more than 10 carbon atoms, normally having an aliphatic or aromatic hydrocarbon chain, or combination thereof, wherein the aliphatic chain is usually of from about 2 to 6 carbon atoms and the aromatic chain is of from about 6 to 12, usually 6 to 10 carbon atoms; L normally has from 0 to 4, when aromatic, usually 1 to 4, more usually 2 to 4 substituents, wherein the substituents may be halo, particularly chloro; non-oxo-carbonyl; thio, including inert sulfur acids, esters and amides; amino, particularly tert-amino of amido; and oxy, wherein the substituents are normally of from 0 to 4 carbon atoms, there being at least two carbon atoms between heteroatoms bonded to saturated carbon atoms;

α is an organic compound, a member of a specific binding pair, either a ligand or receptor;

β is 1, when α is covalently bonded to Ψ or Ψ', and is otherwise 0; the covalent bond normally involves an amido, methylene sec-amino, ether, thioether or azo link;

Ψ is a group terminating in a heteroatom containing functionality when not bonded to α, wherein the terminal heteroatom containing functionality may be bonded directly to a carbon atom of L or through an oligomer of from 1 to 4 units, each unit of 1 to 4, usually 2 to 4 carbon atoms, which units are amino acids, alkyleneamino, or alkyleneoxy groups; the terminal functionality is normally oxo, including oxo-carbonyl and non-oxo-carbonyl; amino; oxy; thio; or active halogen; particularly non-oxo-carbonyl; and ν is one when β is 0 and is otherwise on the average at least one and not more than the molecular weight of α divided by 500, usually divided by 1,000.

Desirably, there are from 2 to 6 chloro substituents on the fluorescent group (in the brackets), bonded at other than the 1,8-positions of the xanthenone. Also, the 4,5-positions may be unsubstituted or one or both, usually both, substituted with bromo, chloro, or alkyl of from 1 to 6, usually 1 to 3 carbon atoms.

The fluorescer compound or conjugate with the organic compound (α) may be linked, covalently or non-covalently to a support. The conjugate may be bound either through the fluoroescer or organic compound. The support will be described in greater detail subsequently.

For the most part, the compounds of this invention having a 9-phenyl will have the following formula:

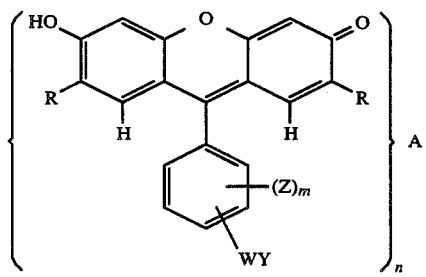

wherein:

R is an aliphatic group of from 1 to 8, usually 1 to 6, more usually 1 to 4, and preferably 1 to 3 carbon atoms, which may be substituted or unsubstituted, aliphatically saturated or unsaturated, particularly alkyl or carboxyalkyl of from 1 to 6, usually 1 to 4 carbon atoms;

Z is carboxy;

W is a bond or divalent radical having from 0 to 16, either 0 or usually 1 to 16 carbon atoms, more usually 1 to 8 carbon atoms and from 0 to 10, usually 2 to 8 heteroatoms, which are chalcogen (oxygen and sulfur) or nitrogen, wherein chalcogen is present bonded solely to carbon (oxy or oxo) and nitrogen is present bonded solely to carbon and hydrogen (amino and amido); carbon is normally aromatic or aliphatic, particularly free of aliphatic unsaturation, having from 0 to 2 sites of ethylenic unsaturation; W is conveniently a monomer or oligomer of units of from 1 to 4 carbon atoms e.g. alkylene, aminoacid, oxyalkylene, aminoalkylene, etc.;

Y may be taken together with A to form an active functionality capable of forming a covalent bond with a heterofunctionality, such as amino, hydroxy, mercapto; that is with those functionalities present on A, when A is not taken together with Y, such as oxo, oxo- and non-oxo-carbonyl, oxy, thio, amino, active halo, active olefin, inorganic acyl group, e.g. sulfonyl, etc. or acts as a linking functionality, being either methylene or heteroatom containing;

A, when not taken together with Y, is a member of a specific binding pair, which is ligand or receptor, wherein the ligand may be haptenic or antigenic, normally being of from about 125 molecular weight to an indefinite upper limit, although for the most part, most ligands will be under 10 million molecular weight, more usually under 2 million molecular weight, with varying ranges depending upon the nature of the ligand or receptor;

m will be 0 to 3, more usually 0 to 2; and n will be 1 when Y and A are taken together and will otherwise be on the average 1 to the molecular weight of A divided by 500, more usually divided by 1,000, and more frequently divided by 2,000, wherein with specific binding pair members over 600,000 molecular weight A will normally be not greater than A divided by 5,000. In addition, there will usually be at least two chloro substituents bonded on any of the available positions where no specific atom is indicated. Also, the 4,5-positions may be substituted as described previously. Furthermore, either the conjugate or the fluorescer precursor may be bonded to a support of at least about 10,000 molecular weight and up to an indefinite molecular weight.

A preferred group of compounds will for the most part have the following formula:

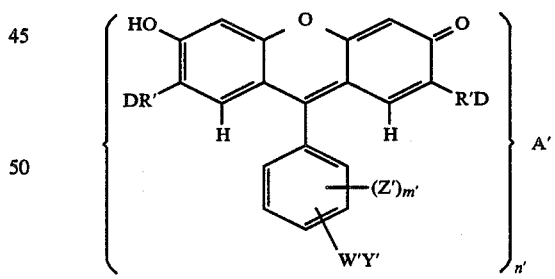

wherein:

R' is alkylene of from 1 to 6, usually 1 to 4, and preferably 1 to 3 carbon atoms;

D is hydrogen or carboxy;

Z' is carboxy;

m' is 0 to 3, usually 0 to 2;

Y' may be taken together with A' to form an active functionally which may be non-oxo-carbonyl, including the sulfur analog thereof, amino bonded to at least one hydrogen atom, mercapto, active ethylene, usually having an α-carbonyl, halomethylcarbonyl, wherein halo is of atomic number 17 to 53, sulfonyl, or the like; when not taken together with A', Y' will be a linking functionality, either methylene or a heteroatom containing linking functionality, usually being an amide, ester, ether or azo link;

W' is a bond or linking group of from 1 to 16, usually 1 to 12, and preferably 1 to 8 atoms other than hydrogen, which are carbon, nitrogen, oxygen or sulfur, preferably carbon, nitrogen and oxygen, there being from 0 to 8 carbon atoms and 0 to 8 heteroatoms, with the number of carbon atoms and heteroatoms being at least 1, wherein nitrogen will be bonded solely to hydrogen and carbon, and will be either amino or amido, oxygen nd sulfur will be bonded solely to carbon as oxy (thio) or oxo (thiono) and carbon is normally aliphatic and usually free of aliphatic unsaturation, generally having from 0 to 1 site of ethylenic unsaturation; W' may be alkylene or alkenylene of from 1 to 8, usually 1 to 4 carbon atoms, oxoalkylene or oxoalkenylene of from 1 to 8, usually 1 to 4 carbon atoms, imino (NH), N-formyl amino acid or N-formyl poly(amino acid) e.g. glycine or polyglycine, there being from about 1 to 4 amino acids, with the terminal carboxy being Y'A', or the like;

n' is 1 when Y' and A' are taken together and otherwise is on the average at least 1 to the molecular weight of A' divided by 500, usually divided by 1,000, more usually divided by 2,000, and when A' is over 500,000 molecular weight, more usually divided by 5,000;

there generally being not more than 5 carboxyl groups, usually not more than 4 carboxyl groups in total, and there being from 0 to 6 chloro groups, preferably 2 to 5 chloro groups bonded to available carbon atoms; and A' is a member of a specific binding pair, a ligand or receptor, wherein the ligand may be haptenic or antigenic, and haptenic ligands will include compounds of interest such as drugs, hormones, pollutants, compounds of interest in processing, agricultural chemicals, metabolites, and the like;

antigens will primarily be proteins, polysaccharides or nucleic acids, individually or in combination with each other or other materials, such as in cells, viruses, phage, or the like. The haptens will normally be from about 125 to 2,000, more usually to 1,000 molecular weight, while the antigens will normally be from about 2,000, more usually 5,000 molecular weight up to an indefinite molecular weight, usually not exceeding 10 million, more usually not exceeding 2 million.

The 4,5-positions are preferably unsubstituted or chloro-substituted.

In addition, the above conjugate may be bonded to a support. Various supports may be employed, both soluble or insoluble, swellable or nonswellable, by aqueous or organic solvents, naturally occurring or synthetic, organic or inorganic, porous or nonporous, or the like. Various polymeric materials include vinyl polymers and copolymers, polysaccharides, silicones, glass, carbon particles, such as graphite or charcoal, metals or metal compounds, poly(amino acids), nucleic acids or the like.

For the most part, the fluorescent compounds of the subject invention employed for conjugation will have the following formula:

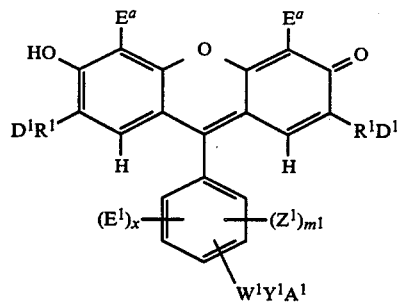

wherein:

$R^1$ is alkylene of from 1 to 6, usually 1 to 4, preferably 1 to 2 carbon atoms;

$D^1$ is hydrogen or carboxy, preferably hydrogen;

$Z^1$ is carboxy;

$E^a$ is hydrogen, alkyl of from 1 to 6, usually 1 to 3 carbon atoms, or chloro;

$E^1$ is chloro;

$W^1$ is a bond or linking group of from 1 to 12, usually 1 to 8 atoms other than hydrogen, and generally 1 to 8, usually 1 to 6 atoms in the chain wherein the atoms are carbon, nitrogen, oxygen and sulfur, particularly carbon, nitrogen and oxygen, wherein the carbon is aliphatic, the nitrogen is present as amido or amino, particularly amino bonded solely to carbon, and oxygen and sulfur are bonded solely to carbon and are oxy or oxo or the sulfur analogs thereof:

$W^1$ will generally be aliphatic, being saturated or unsaturated, normally saturated, having from 0 to 1 site of ethylenic unsaturation, alkylene or alkenylene of from 1 to 8, usually 1 to 4 carbon atoms, N-formyl amino acid of N-formyl poly(amino acid), where the terminal carboxy is derived from $Y^1A^1$, amino, mercapto, or the like;

$Y^1A^1$ are taken together to form a functionality for linking, wherein $Y^1A^1$ are bonded solely to carbon or nitrogen, with the proviso that when $Y^1$ and $A^1$ are bonded to nitrogen, $Y^1A^1$ are carbonyl, including the nitrogen and sulfur analogs thereof and can be doubly bonded to nitrogen;

$Y^1A^1$ can be non-oxo-carbonyl, haloacetyl, halogen of atomic no. 9 to 53, particularly chloro or bromo, maleimido, mercapto, amino, or inorganic acyl, having phosphorous or sulfur as the central atom;

$m^1$ is 0 to 3, usually 0 to 2, there usually being not more than a total of 5 carboxyl groups in the molecule, usually not more than a total of 4 carboxyl groups, and preferably not more than about 2 carboxyl groups, other than $Y^1A^1$;

x is 0 to 4, preferably 2 to 4, there generally being not more than a total of 6 chloro groups in the molecule, usually not more than a total of 4 chloro groups, wherein x plus $m^1$ is not greater than 4.

For the most part, the compositions of this invention when bonded to ligand or support will have the following formula:

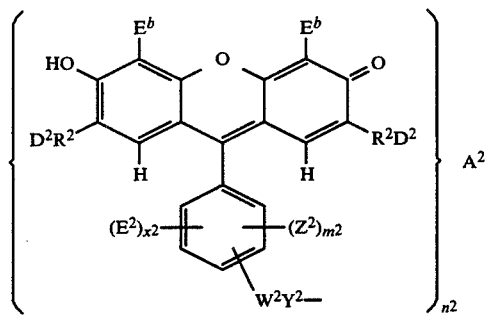

wherein:
$E^b$ is hydrogen or chloro;
$E^2$ is chloro;
$Z^2$ is carboxy;
$R^2$ is alkylene of from 1 to 6, usually 1 to 3, preferably 1 to 2 carbon atoms;
$D^2$ is hydrogen or carboxy, preferably hydrogen;
$W^2$ is a bond or linking chain, when a linking chain being of from 1 to 12, usually of from 1 to 10, and preferably of from about 1 to 8 atoms other than hydrogen, having from about 1 to 10, usually from about 1 to 8, and preferably from about 1 to 6 atoms in the chain or spacer arm, wherein the atoms are carbon, oxygen, nitrogen and sulfur, particularly carbon, oxygen and nitrogen in the spacer arm, wherein oxygen and sulfur are bonded solely to carbon, as oxy or oxo, and nitrogen is bonded solely to carbon and hydrogen, namely amino and amido, wherein heteroatoms bonded to saturated carbon atoms are separated by at least two carbon atoms;
$W^2$ is particularly alkylene, carboxamidoalkylene, wherein alkylene is of from about 1 to 2 carbon atoms-$(-CONHC_{1-2}-)_a$, wherein $a$ is in the range of from about 1 to 4, usually 1 to 3;
$Y^2$ is non-oxo-carbonyl, carbamyl, thiocarbamyl, methylene, amino, or thio, particularly a functionality having a non-oxo-carbonyl group or sulfur analog thereof;
$x^2$ is 0 to 4;
$m^2$ is 0 to 3, preferably 1 to 2;
$n^2$ is 1 to the molecular weight of $A^2$ divided by 500, usually divided by 1,000, more usually divided by 2,000, wherein when $A^2$ is a ligand of between about 125 to 2,000 molecular weight, $n^2$ will generally be of from about 1 to 20, when $A^2$ is a ligand of from about 2,000 to 600,000 molecular weight, $n^2$ will generally be in the range of about 1 to 100, more usually in the range of about 2 to 50; and
$A^2$ is a ligand of at least about 125 molecular weight and may be 10 million or more molecular weight, which is haptenic or antigenic, wherein haptens are from about 125 to 2,000 molecular weight and antigens will generally range from about 5,000 to 10 million molecular weight, more usually from about 5,000 to 2 million molecular weight and frequently from about 5,000 to 600,000 molecular weight, the ligand being a member of a specific binding pair, which comprises a compound having at least 1 determinant or epitopic site and a receptor which is capable of recognizing the determinant size or $A^2$ is a receptor of from about 10,000 to 1 million molecular weight.

Finally, in some instances it may be desirable to have the fluorescent compound or the conjugate of the fluorescent compound with ligand, bonded to a support, where the linkage may be derived from either the fluorescent compound or the ligand, normally the ligand. In this situation, the linking group may be any convenient functionality which is present on the fluorescent compound or the ligand or a functionality which may be introduced, particularly on the ligand. These compositions will for the most part have the following formula, where the symbols are derived from the previous formula for the conjugate for the most part:

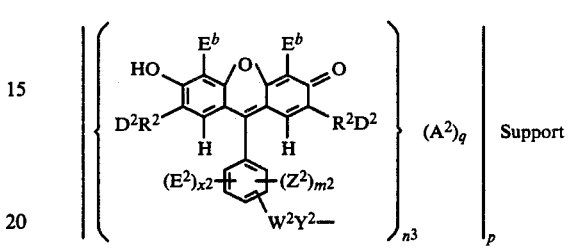

wherein:
all of the symbols have been defined previously, except for:
$n^3$ which is at least 1 and up to the molecular weight of $A^2$ divided by 500, usually 1000, more usually 1,500, with the proviso that when $q$ is 0, $n^3$ is 1;
$q$ which is 0 or 1;
$p$ which is at least 1 and of up to the molecular weight of the support divided by 500, more usually the molecular weight of the support divided by 1,000, wherein when the molecular weight of the support exceeds 500,000, $p$ will normally be not greater than the molecular weight of the support divided by 5,000, more usually divided by 10,000; and Support intends a macromolecular support of at least about 10,000 molecular weight, which may be naturally occurring or synthetic, having a plurality of functionalities for linking e.g. carboxy, hydroxy, or amino, usually being a polymer, such as a polysaccharide or an addition polymer; the support being bonded to the conjugate by any convenient functionality remaining an $A^2$ or the conjugate in the brackets, the particular manner of linking not being a significant aspect of the subject invention. For example, if $A^2$ is a poly(amino acid), carboxylic groups on the support can be used for amide formation or maleimide groups may be introduced and linked to mercapto groups.

Quite obviously, the compounds of the subject invention can be modified so as not to be within the above formulas, without significantly affecting the properties of the compounds. For example, one or more of the acidic anionic groups could be esterified or amidified, or alkyl groups can be substituted on the phenyl, as well as other groups, such as cyano, nitro, or the like. However, these changes will in most cases require additional synthetic steps which are not warranted by the degree of enhancement, if any, in the spectroscopic or chemical properties of the resulting product.

Turning now to a consideration of the individual components of the subject compositions, the fluorescein derivatives will be considered first. The following is a list of illustrative fluorescein derivatives coming within the scope of the subject invention.

TABLE I 2,7-dimethyl-4,5-dichloro-9-(2',4',5'-tricarboxyphenyl)-6-hydroxy-3-xanthen-3-one
2,7-diethyl-4,5-dichloro-9-(2',4',5'-tricarboxy-3',6'-dichlorophenyl)-6-hydroxy-3H-xanthen-3-one
2,7-dihexyl-9-(2',4',5'-tricarboxyphenyl)-6-hydroxy-3H-xanthen-3-one
2,7-dimethyl-4,5-dichloro-9-(2'-carboxy-4'-isothiocyanato-3',5'-dichlorophenyl)-6-hydroxy-3H-xanthen-3-one
2,7-dimethyl-9-(2'-carboxy-4'-isocyanato-3',5',6'-trichlorophenyl)-6-hydroxy-3H-xanthen-3-one
2,7-dimethyl-9-(4'-carboxy-5'-carboxylphenyl)-glycylglycylglycine amide-6-hydroxy-3H-xanthen-3-one
2,7-di(carboxymethyl)-9-(4',5',-dicarboxy-2',3',6'-trichlorophenyl)-6-hydroxy-3H-xanthen-3-one
2,7-di(carboxypropyl)-4,5-dichloro-9-(3',4'-dicarboxyphenyl)-6-hydroxy-3H-xanthen-3-one
2,7-diethyl-9-(2'-carboxy-4'-amino-3',5'-dichlorophenyl)-6-hydroxy-3H-xanthen-3-one
2,7-dimethyl-9-(2'-carboxy-4'-mercaptophenyl)-6-hydroxy-3H-xanthen-3-one
2,7-dimethyl-9-(2'-carboxy-4'-carboxymethylphenyl)-6-hydroxy-3H-xanthen-3-one
2,7-dimethyl-9-(2'-carboxy-4'-(4''-carboxybutyl)-phenyl)-6-hydroxy-3H-xanthen-3-one
2,7-dimethyl-4,5-dichloro-9-(2',4'-dicarboxy-5'-(carboxamidomethylene)phenyl)-6-hydroxy-3H-xanthen-3-one
2,7-dimethyl-4,5-dichloro-9(3'-carboxypropyl)-6-hydroxy-3H-xanthen-3-one.

As indicated previously, the fluorescein derivatives of the subject invention will be conjugated with ligands and/or supports. The following is a description of the applicable ligands.

Analyte

The ligand analytes of this invention are characterized by being monoepitopic or polyepitopic. The polyepitopic ligand analytes will normally be poly(amino acids) i.e. polypeptides and proteins, polysaccharides, nucleic acids, and combinations thereof. Such combinations of assemblages include bacteria, viruses, chromosomes, genes, mitochondria, nuclei, cell membranes, and the like.

For the most part, the polyepitopic ligand analytes employed in the subject invention will have a molecular weight of at least about 5,000, more usually at least about 10,000. In the poly(amino acid) category, the poly(amino acids) of interest will generally be from about 5,000 to 5,000,000 molecular weight, more usually from about 20,000 to 1,000,000 molecular weight; among the hormones of interest, the molecular weights will usually range from about 5,000 to 60,000 molecular weight.

The wide variety of proteins may be considered as to the family of proteins having similar structural features, proteins having particular biological functions, proteins related to specific microorganisms, particularly disease causing microorganisms, etc.

The following are classes of proteins related by structure:
protamines
histones
albumins
globulins
scleroproteins
phosphoproteins
mucoproteins
chromoproteins
lipoproteins
nucleoproteins
glycoproteins
proteoglycans
unclassified proteins, e.g. somatotropin, prolactin, insulin, pepsin A number of proteins found in the human plasma are important clinically and include:
Prealbumin
Albumin
$\alpha_1$-Lipoprotein
$\alpha_1$-Acid glycoprotein
$\alpha_1$-Antitrypsin
$\alpha_1$-Glycoprotein
Transcortin
4.6S-Postalbumin
Tryptophan-poor
  $\alpha_1$-glycoprotein
$\alpha_1$X-Glycoprotein
Thyroxin-binding globulin
Inter-$\alpha$-trypsin-inhibitor
Gc-globulin
  (Gc 1-1)
  (Gc 2-1)
  (Gc 2-2)
Haptoglobin
  (Hp 1-1)
  (Hp 2-1)
  (Hp 2-2)
Ceruloplasmin
Cholinesterase
$\alpha_2$-Lipoprotein(s)
Myoglobin
C-Reactive Protein
$\alpha_2$-Macroglobulin
$\alpha_2$-HS-glycoprotein
Zn-$\alpha_2$-glycoprotein
$\alpha_2$-Neuramino-glycoprotein
Erythropoietin
$\beta$-lipoprotein
Transferrin
Hemopexin
Fibrinogen
Plasminogen
$\beta_2$-glycoprotein I
$\beta_2$-glycoprotein II
Immunoglobulin G
  (IgG) or $\gamma$G-globulin
Mol. formula:
  $\gamma_2\kappa_2$ or $\gamma_2\lambda_2$
Immunoglobulin A (IgA)
  or $\gamma$A-globulin
Mol. formula:
  $(\alpha_2\kappa_2)^n$ or $(\alpha_2\lambda_2)^n$
Immunoglobulin M
  (IgM) or $\gamma$M-globulin
Mol. formula:
  $(\mu_2\mu_2)^5$ or $(\mu_2\lambda_2)^5$
Immunoglobulin D(IgD)
  or $\gamma$D-Globulin ($\gamma$D)
Mol. formula:
  $(\delta_2\kappa_2)$ or $\delta_2\lambda_2)$
Immunoglobulin E (IgE)
  or $\gamma$E-Globulin ($\gamma$E)
Mol. formula:

($\epsilon_2\kappa_2$) or ($\epsilon_2\lambda_2$)
Free $\kappa$ and $\lambda$ light chains
Complement factors:
C'1
   C'1q
   C'1r
   C'1s
C'2
C'3
   $\beta_1$A
   $\alpha_2$D
C'4
C'5
C'6
C'7
C'8
C'9
Important blood clotting factors include:

BLOOD CLOTTING FACTORS

| International designation | Name |
|---|---|
| I | Fibrinogen |
| II | Prothrombin |
| IIa | Thrombin |
| III | Tissue thromboplastin |
| V and VI | Proaccelerin, accelerator globulin |
| VII | Proconvertin |
| VIII | Antihemophilic globulin (AHG) |
| IX | Christmas factor, plasma thromboplastin component (PTC) |
| X | Stuart-Prower factor, autoprothrombin III |
| XI | Plasma thromboplastin antecedent (PTA) |
| XII | Hagemann factor |
| XIII | Fibrin-stabilizing factor |

Important protein hormones include:

Peptide and Protein Hormones

Parathyroid hormone
   (parathromone)
Thyrocalcitonin
Insulin
Glucagon
Relaxin
Erythropoietin
Melanotropin
   (melanocyte-stimulating hormone; intermedin)
Somatotropin
   (growth hormone)
Corticotropin
   (adrenocorticotropic hormone)
Thyrotropin
Follicle-stimulating hormone
Luteinizing hormone
   (interstitial cell-stimulating hormone)
Luteomammotropic hormone
   (luteotropin, prolactin)
Gonadotropin
   (chorionic gonadotropin)

Tissue Hormones

Secretin
Gastrin
Angiotensin I and II
Bradykinin
Human placental lactogen

Peptide Hormones from the Neurophypophysis

Oxytocin
Vasopressin
Releasing factors (RF)
   CRF, LRF, TRF, Somatotropin-RF,
   GRF, FSH-RF, PIF, MIF Other polymeric materials of interest are mucopolysaccharides and polysaccharides.

Illustrative antigenic polysaccharides derived from microorganisms are as follows:

| Species of Microorganisms | Hemosensitin Found in |
|---|---|
| Streptococcus pyogenes | Polysaccharide |
| Diplococcus pneumoniae | Polysaccharide |
| Neisseria meningitidis | Polysaccharide |
| Neisseria gonorrheae | Polysaccharide |
| Corynebacterium diptheriae | Polysaccharide |
| Actinobacillus mallei; Actinobacillus whitemori | Crude extract |
| Francisella tularensis | Lipopolysaccharide Polysaccharide |
| Pasteurella pestis | |
| Pasteurella pestis | Polysaccharide |
| Pasteurella multocida | Capsular antigen |
| Brucella abortus | Crude extract |
| Haemophilus influenzae | Polysaccharide |
| Haemophilus pertussis | Crude |
| Treponela reiteri | Polysaccharide |
| Veillonella | Lipopolysaccharide |
| Erysipelothrix | Polysaccharide |
| Listeria monocytogenes | Polysaccharide |
| Chromobacterium | Lipopolysaccharide |
| Mycobacterium tuberculosis | Saline extract of 90% phenol extracted mycobacteria and polysaccharide fraction of cells and turberculin |
| Klebsiella aerogenes | Polysaccharide |
| Klebsiella cloacae | Polysaccharide |
| Salmonella typhosa | Lipopolysaccharide, Polysaccharide |
| Salmonella typhi-murium; Salmonella derby Salmonella pullorum | Polysaccharide |
| Shigella dysenteriae Shigella flexneri | Polysaccharide |
| Shigella sonnei | Crude, Polysaccharide |
| Rickettsiae | Crude extract |
| Candida albicans | Polysaccharide |
| Entamoeba histolytica | Crude extract |

The microorganisms which are assayed may be intact, lysed, ground or otherwise fragmented, and the resulting composition or portion, e.g. by extraction, assayed. Microorganisms of interest include:

Corynebacteria

*Corynebacterium diptheriae*

Pneumococci

*Diplococcus pneumoniae*

Streptococci

*Streptococcus pyogenes*
*Streptococcus salivarus*

Staphylococci

*Staphylococcus aureus*
*Staphylococcus albus*

Neisseriae

*Neisseria meningitidis*
*Neisseria gonorrheae*

| Enterobacteriaciae | |
|---|---|
| *Escherichia coli* | |
| *Aerobacter aerogenes* | } The coliform |
| *Klebsiella pneumoniae* | bacteria |
| *Salmonella typhosa* | |
| *Salmonella choleraesuis* | } The *Salmonellae* |
| *Salmonella typhimurium* | |
| *Shigella dysenteriae* | |
| *Shigella schmitzii* | |
| *Shigella arabinotarda* | } The *Shigellae* |
| *Shigella flexneri* | } The *Shigellae* |
| *Shigella boydii* | |
| *Shigella Sonnei* | |
| Other *enteric bacilli* | |
| *Proteus vulgaris* | |
| *Proteus mirabilis* | } *Proteus* species |
| *Proteus morgani* | |
| *Pseudomonas aeruginosa* | |
| *Alcaligenes faecalis* | |
| *Vibrio cholerae* | |
| Hemophilus-Bordetella group | |
| *Hemophilus influenzae*, | *H. ducreyi* |
| | *H. hemophilus* |
| | *H. aegypticus* |
| | *H. parainfluenzae* |
| *Bordetella pertussis* | |

Pasteurellae

*Pasteurella pestis*
*Pasteurella tulareusis*

Brucellae

*Brucella melitensis*
*Brucella abortus*
*Brucella suis*

Aerobic Spore-forming Bacilli

*Bacillus anthracis*
*Bacillus subtilis*
*Bacillus megaterium*
*Bacillus cereus*

Anaerobic Spore-forming Bacilli

*Clostridium botulinum*
*Clostridium tetani*
*Clostridium perfringens*
*Clostridium novyi*
*Clostridium septicum*
*Clostridium histolyticum*
*Clostridium tertium*
*Clostridium bifermentans*
*Clostridium sporogenes*

Mycobacteria

*Mycobacterium tuberculosis hominis*
*Mycobacterium bovis*
*Mycobacterium avium*
*Mycobacterium leprae*
*Mycobacterium paratuberculosis*

Actinomycetes (fungus-like bacteria)

*Actinomyces israelii*
*Actinomyces bovis*
*Actinomyces naeslundii*
*Nocardia asteroides*
*Nocardia brasiliensis*

| The *Spirochetes* | |
|---|---|
| *Treponema pallidum* | *Spirillum minus* |
| *Treponema pertenue* | *Streptobacillus moniliformis* |
| *Treponema carateum* | |
| *Borrelia recurrentis* | |
| *Leptospira icterohemorrhagiae* | |
| *Leptospira canicola* | |

Mycoplasmas

*Mycoplasma pneumoniae*

Other pathogens

*Listeria monocytogenes*
*Erysipelothrix rhusiopathiae*
*Streptobacillus moniliformis*
*Donvania granulomatis*
*Bartonella bacilliformis*

Rickettsiae (bacteria-like parasites)

*Rickettsia prowazekii*
*Rickettsia mooseri*
*Rickettsia rickettsii*
*Rickettsia conori*
*Rickettsia australis*
*Rickettsia sibiricus*
*Rickettsia akari*
*Rickettsia tsutsugamushi*
*Rickettsia burnetii*
*Rickettsia quintana*

Chlamydia (unclassifiable parasites bacterial/viral)

Chlamydia agents (naming uncertain)

Fungi

*Cryptococcus neoformans*
*Blastomyces dermatidis*
*Histoplasma capsulatum*
*Coccidioides immitis*
*Paracoccidioides brasiliensis*
*Candida albicans*
*Aspergillus fumigatus*
*Mucor corymbifer* (*Absidia corymbifera*)

| | |
|---|---|
| *Rhizopus oryzae* | |
| *Rhizopus arrhizus* | } Phycomycetes |
| *Rhizopus nigricans* | |

*Sporotrichum schenkii*
*Fonsecaea pedrosoi*
*Fonsecaea compacta*
*Fonsecaea dermatidis*
*Cladosporium carrionii*
*Phialophora verrucosa*
*Aspergillus nidulans*
*Mandurella mycetomi*

*Madurella grisea*
*Allescheria boydii*
*Phialosphora jeanselmei*
*Microsporum gypseum*
*Trichophyton mentagrophytes*
*Keratinomyces ajelloi*
*Microsporum canis*
*Trichophyton rubrum*
*Microsporum andouini*

Viruses

Adenoviruses

Herpes Viruses

*Herpes simplex*
Varicella (Chicken pox)
*Herpes Zoster (Shingles)*
Virus B
Cytomegalovirus

Pox Viruses

Variola (smallpox)
Vaccinia
*Poxvirus bovis*
Paravaccinia
*Molluscum contagiosum*

Picornaviruses

Poliovirus
Coxsackievirus
Echoviruses
Rhinoviruses

Myxoviruses

Influenza (A, B, and C)
Parainfluenza (1-4)
Mumps Virus
Newcastle Disease Virus
Measles Virus
Rinderpest Virus
Canine Distemper Virus
Respiratory Syncytial Virus
Rubella Virus

Arboviruses

Eastern Equine Eucephalitis Virus
Western Equine Eucephalitis Virus
Sindbis Virus
Chikugunya Virus
Semliki Forest Virus
Mayora Virus
St. Louis Encephalitis Virus
California Encephalitis Virus
Colorada Tick Fever Virus
Yellow Fever Virus
Dengue Virus

Reoviruses

Reovirus Types 1-3

Hepatitis

Hepatitis A Virus
Hepatitis B Virus

Tumor Viruses

Rauscher Leukemia Virus
Gross Virus
Maloney Leukemia Virus

The monoepitopic ligand analytes will generally be from about 100 to 2,000 molecular weight, more usually from 125 to 1,000 molecular weight. The analytes of interest include drugs, metabolites, pesticides, pollutants, and the like. Included among drugs of interest are the alkaloids. Among the alkaloids are morphine alkaloids, which includes morphine, codeine, heroin, dextromethorphan, their derivatives and metabolites; cocaine alkaloids, which includes cocaine and benzoyl ecgonine, their derivatives and metabolites; ergot alkaloids, which includes the diethylamide of lysergic acid; steroid alkaloids; iminazoyl alkaloids; quinazoline alkaloids, isoquinoline alkaloids; quinoline alkaloids; which includes quinine and quinidine; diterpene alkaloids; their derivatives and metabolites.

The next group of drugs includes steroids, which includes the estrogens, gestogens, androgens, andrenocortical steroids, bile acids, cardiotonic glycosides and aglycones, which includes digoxin and digoxigenin, saponins and sapogenins, their derivatives and metabolites. Also included are the steroid mimetic substances, such as diethylstilbestrol.

The next group of drugs is lactams having from 5 to 6 annular members, which include the barbiturates, e.g. phenobarbital and secobarbital, diphenylhydantonin, primidone, ethosuximide, and their metabolites.

The next group of drugs is aminoalkylbenzenes, with alkyl of from 2 to 3 carbon atoms, which includes the amphetamines, catecholamines, which includes ephedrine, L-dopa, epinephrine, narceine, papaverine, their metabolites.

The next group of drugs is aminoalkylbenzenes, with alkyl of from 2 to 3 carbon atoms, which includes ephedrine, L-dopa, epinephrine, narceine, papverine, their metabolites and derivatives.

The next group of drugs is benzheterocyclics which include oxazepam, chlorpromazine, tegretol, imipramine, their derivatives and metabolites, the heterocyclic rings being azepines, diazepines and phenothiazines.

The next group of drugs is purines, which includes theophylline, caffeine, their metabolites and derivatives.

The next group of drugs includes those derived from marijuana, which includes cannabinol and tetrahydrocannabinol.

The next group of drugs includes the vitamins such as A, B, e.g. $B_{12}$, C, D, E and K, folic acid, thiamine.

The next group of drugs is prostaglandins, which differ by the degree and sites of hydroxylation and unsaturation.

The next group of drugs is antibiotics, which include penicillin, chloromycetin, actinomycetin, tetracycline, terramycin, their metabolites and derivatives.

The next group of drugs is the nucleosides and nucleotides, which include ATP, NAD, FMN, adenosine, guanosine, thymidine, and cytidine with their appropriate sugar and phosphate substituents.

The next group of drugs is miscellaneous individual drugs which include methadone, meprobamate, serotonin, meperidine, amitriptyline, nortriptyline, lidocaine, procaineamide, acetylprocaineamide, propranolol, griseofulvin, valproic acid, butyrophenones, antihistamines, anticholinergic drugs, such as atropine, their metabolites and derivatives.

The next group of compounds is amino acids and small peptides which include polyiodothyronines e.g. thyroxine, and triiodothyronine, oxytocin, ACTH, angiotensin, met-and leu-enkephalin their metabolites and derivatives.

Metabolites related to diseased states include spermine, galactose, phenylpyruvic acid, and porphyrin Type 1.

The next group of drugs is aminoglycosides, such as gentamicin, kanamicin, tobramycin, and amikacin.

Among pesticides of interest are polyhalogenated biphenyls, phosphate esters, thiophosphates, carbamates, polyhalogenated sulfenamides, their metabolites and derivatives.

For receptor analytes, the molecular weights will generally range from 10,000 to $2 \times 10^6$, more usually from 10,000 to $10^6$. For immunoglobulins, IgA, IgG, IgE and IgM, the molecular weights will generally vary from about 160,000 to about $10^6$. Enzymes will normally range from about 10,000 to 6000,000 in molecular weight. Natural receptors vary widely, generally being at least about 25,000 molecular weight and may be $10^6$ or higher molecular weight, including such materials as avidin, thyroxine binding globulin, thyroxine binding prealbumin, transcortin, etc.

In many applications for the subject fluorescein derivatives, it will be desirable to have the ligand bonded to a support, either directly, through the intermediacy of a ligand, or directly to the support, while bound to a ligand.

A wide variety of supports may be employed. The particles or supports can be derived from naturally occurring materials, naturally occurring materials which are synthetically modified and synthetic materials. Of particular interest are polysaccharides, particularly crosslinked polysaccharides, such as agarose, which is available as Sepharose, dextran, available as Sephadex and Sephacyl, cellulose, starch, and the like. Other materials include polyacrylamides, polystyrene, polyvinyl alcohol, copolymers of hydroxyethyl methacrylate and methyl methacrylate, silicones, glasses, available as Bioglas, nucleic acids, poly(amino acids), cells or the like. In addition to solid particles, liquid particles may also be employed having a lipophilic or amphiphilic membrane, which serves to contain an internal fluid and define a space. Such particles include vesicles, cells and liposomes.

The particles may be porous or nonporous, swellable or nonswellable by aqueous or organic media, normally having a variety of functionalities, such as hydroxyl, amino or carboxy, either bonded directly to the backbone or by means of a spacer arm, crosslinked or noncrosslinked, smooth or rough surface, or the like.

The porous particles may have a wide variety of cut off sizes, generally varying from about 10,000 to many million molecular weight, usually not exceeding 20 million molecular weight.

As already indicated, a wide variety of linking chains may be employed between the fluorescein compound and the ligand and/or support. The choice of linking group will vary widely, depending upon the available functionalities or functionalities which may be readily introduced, the desired length of the linking arm, the desirabilty of having the linking arm provide for a particular environment, chemical property or physical property, e.g. positively or negatively charged, solubility enhancement, dipole effects, or the like.

The following table indicates a variety of linking groups which may be employed for linking the fluorescein compound to the ligand:

TABLE II

| Fluorescein functionality | Linking group | Ligand functionality |
| --- | --- | --- |
| —CO$_2$H | —(NHGCO)$_g$— | —NH$_2$ |
| —CO$_2$H or —SO$_3$H | —(NHG'NH)$_{g'}$NHG'NH— —NHG'N(CH$_2$CH$_2$)$_2$NG'NH— | —CO$_2$H |
| —SH | $\begin{array}{c} \text{CO} \\ \diagdown \\ \text{NG'NH}_2 \\ \diagup \\ \text{CO} \end{array}$ | —CO$_2$H |
| —COCH$_2$halo | $\left.\begin{array}{c}-\text{O}\\-\text{S}\end{array}\right\}$ GNH | —CO$_2$H |
| —NH$_2$ | —COGCO— | —NH$_2$ | wherein:

G is alkylene of from 1 to 8, usually 1 to 6 carbon atoms, G' is alkylene of from 2 to 6, usually 2 to 4 carbon atoms, and g and g' are 1 to 6, usually 1 to 4. It is understood that the above table is merely illustrative of the more common linking groups, other linking groups being available in special situations. For example, where phenolic groups are present, such as tyrosyl, aryl diazonium functionalities may be employed. Furthermore, it is understood that the functionalities for the fluorescein and ligand may be reversed, with concomitant reversal of the direction of the linking group.

The subject compounds have many desirable properties. The products have significant water solubility which allow them to be conjugated to a wide variety of polypeptides, without significantly adversely affecting the water solubility of the polypeptide, nor having the polypeptide adversely affect the spectroscopic properties of the subject compounds.

As for the spectroscopic properties of the compounds, the compounds absorb at relatively long wavelengths, generally in excess of 500 nm, more usually in excess of 510 nm. Thus, naturally occurring fluorescence which may be encountered when working with physiological fluids is substantially avoided by employing exciting light at a wavelength range which does not significantly excite the naturally occurring fluorescers. In addition, the compounds have relatively sharp absorption peaks and emission peaks. Because of this, efficient overlap can be obtained between fluorescers and quenchers which allow for efficient quenching up to distances of about 70 Å. The fluorescing compounds also have large Stokes shifts, so that the absorption band and emission band peaks are separated by at least 10 nm, frequently by at least 15 nm. The large Stokes shifts minimize background interference with the observed fluorescence.

The compounds of the subject invention are prepared in accordance with conventional means. The appropriate resorcinol and carboxylic acid or anhydride are combined in the presence of a Lewis acid e.g. zinc chloride, and the mixture heated at an elevated temperature for a sufficient time to provide the desired product. The product may then be purified by conventional means.

The subject compounds find a wide variety of applications, particularly for use as conjugates to ligands and/or supports in protein binding assays. The conjugates can be used for determining qualitatively, semiquantitatively or quantitatively the presence of a compound of interest in a sample. Where compounds are to be detected in physiological fluids, the fluids may include serum, urine, saliva, lymph or the like. Where the compound of interest is involved in chemical processing or ecological concerns, the sample may involve an aqueous medium, an organic medium, soil, inorganic mixtures, or the like.

For use in immunoassays or in other diagnostic situations, the spectroscopically active compounds of this invention will be conjugated to a compound of interest, including a receptor for an analyte or a ligand. (By receptor is intended any molecule which specifically binds to a spatial and polar molecular organization, while a ligand is an organic molecule having such organization.) The analyte will normally be haptenic or antigenic. Where these compounds do not have available functionalities for linking, they will be modified to introduce such a functionality, while still retaining the immunological properties in the resulting product. Those compounds which are analogs of the analyte, which analyte may also be referred to as a ligand, will be referred to as ligand analogs.

As indicated previously, the compounds of this invention may be conjugated to compounds which may be measured by known immunoassay techniques. The resulting conjugates are reagents which compete in an assay medium for the compound of interest or analyte in a sample. Therefore, the conjugate retains a sufficient proportion of the structure of the compound of interest to be able to compete with the compound of interest for receptor, usually an antibody.

The analytes or their analogs, receptors or ligands, which are conjugated to the spectroscopically active compounds of this invention are characterized by being monoepitopic or polyepitopic.

The assays will normally involve a change of spectroscopic properties due to a change in environment about the spectroscopically active compound or the bringing together of a fluorescer-quencher pair within sufficient proximity for the quencher to interact with the fluorescer. Alternatively, methods can be employed which involve the separation of associated and unassociated fluorescer and the detection of the fluorescer in one or both of the fractions.

In a first assay, steric exclusion is involved, in that receptors or antibodies for the ligand and for the fluorescer are employed, where simultaneous binding of the receptor for the ligand and receptor for the fluorescer is inhibited. Furthermore, when the receptor for the fluorescer (antifluorescer) is bound to the fluorescer, the fluorescence of the fluorescer is substantially diminished. Further reduction if not complete inhibition of fluorescence can be achieved by conjugation of quencher to the antifluorescer. This assay is extensively described in U.S. Pat. No. 3,998,943, issued Dec. 21, 1976. The fluorescein which is employed there may be substituted with the fluorescent compounds of the subject invention. The assay is described in Columns 3–5 of the subject patent, which description is incorporated herein by reference.

Generally, the method involves combining the samples suspected of containing the analyte, the conjugate of the ligand and fluorescer, anti-fluorescer, and receptor for ligand or antiligand, when ligand is the analyte. The materials are combined in an aqueous medium at a pH in the range of about 5 to 10, usually in the range of about 6 to 9, at a temperature in the range of about 10° to 45° C. and the fluorescence determined either as a rate or equilibrium mode, readings being taken within about 1 second to 1 hour after all materials have been combined for a rate mode, while for an equilibrium mode, readings may be taken for as long as up to about 24 hours or longer.

In the next immunoassay technique, a fluorescer-quencher pair is employed, where one of the members of the pair is conjugated to a member of a specific binding pair, ligand and antiligand, and the other chromophor member is bound to the same or different member of the specific binding pair. For example, the fluorescer and the quencher may be bound to different molecules of antiligand, so that when the two conjugated antiligands are brought together with antigen, the fluorescer and quencher are brought within quenching distance. Alternatively, one could bind one of the chromogens to the ligand and the other chromogen to the antiligand. This assay is extensively described in U.S. Pat. No. 3,996,345. The assay technique is described beginning with Col. 17 and ending at Col. 23, which description is incorporated herein by reference. The ratios of chromogen to ligand and receptor is described in Cols. 4–6, which description is incorporated herein by reference.

The assay is carried out in substantially the same manner as described above, except that in this assay, the fluorescer conjugates and quencher conjugates are added in conjunction with the sample and the fluorescence determined in comparison to an assay medium having a known amount of the analyte.

Other techniques may also be employed with the subject compounds, such as techniques involving heavy atom quenching as described in co-pending application Ser. No. 824,576, filed Aug. 13, 1977 or other assay techniques where a fluorescent molecule is desired which emits light at a wavelength substantially above the light emitted by fluorescent compounds naturally present in physiological fluids or other samples to be analyzed.

Finally, the subject conjugates may be used in conjunction with supports as described in U.S. patent application Ser. No. 964,099, filed Nov. 24, 1978. These assays are predicated upon having the fluorescer molecule available in bulk solution for interaction with a signal modulator or bound to a particle, where the particle environment prevents the interaction. Alternatively, the particle can provide an environment which modulates the fluorescent signals when the fluorescer conjugate is bound to the particle.

EXPERIMENTAL

The following examples are offered by way of illustration and not by way of limitation.

(All temperatures not otherwise indicated are centigrade. All parts and percents not otherwise indicated are by weight, except for mixtures of liquids which are by volume. The following abbreviations are employed. TLC—thin layer chromatography; THF—tetrahydrofuran; DCC—dicyclohexyl carbodiimide; NHS—N-hydroxy succinimide; $T_3$—triiodothyronine.

EXAMPLE I

Preparation of 2,7-dimethyl-9-(3',4'-dicarboxy-2',5',6'-trichlorophenyl)-6-hydroxy-3H-xanthen-3-one A. 4-Methyl phthalic anhydride (20.0 g) was dissolved in 20% fuming sulphuric acid (25 ml) and powdered iodine (0.5 g) added. The mixture was heated to 90°–100° and chlorine gas bubbled through the solution continuously. After 24 hrs heating, 0.5 g more of iodine was added and the heating continued for 24 hrs more. After 2 days of heating, a white solid had precipitated out. The solution was cooled and diluted in 100 ml of ice-cold water and filtered to yield a white solid. The solid was washed with cold water (20 ml) and dried in vacuo. A sample of the product 3,5,6-trichloro-4-methylphthalic acid and anhydride (I) was hydrolyzed to yield a white powder m.p 226°–8°.

B. (I) (20 g, 0.075 moles) was placed in a 1-liter, 3-neck flask equipped with mechanical stirrer and a water condenser and 400 ml 10% $K_2CO_3$ added. The slurry was refluxed in an oil bath at 120° until all the solid had dissolved (about 1 hr). After adding 10 ml tert-butanol, 33.0 g (0.2 moles) powdered $KMnO_4$ was added in portions to the hot stirring solution. Care was taken to avoid accumulation of $KMnO_4$. An additional 100 ml of 10% $K_2CO_3$ was used to wash in the $KMnO_4$. After all $KMnO_4$ had been added, the reaction was checked by TLC. [TLC was taken by the following procedure: A sample of the reaction mixture was acidified with 6M $H_2SO_4$; the excess $KMnO_4$ was reacted with a saturated solution of oxalic acid; the clear solution was extracted with ether. The ether solution was reacted with an ether solution of diazomethane and concentrated under $N_2$. TLC was taken of the methyl ester in 100% benzene; Rf=0.3. The Rf of the methyl ester of the diacid derived from I was 0.5.]

The reaction was stopped when all the diacid was gone by TLC. The tert-butanol was distilled off. The stirring slurry was acidified with 6M $H_2SO_4$ to pH1. The excess $KMnO_4$ was removed by reaction with solid oxalic acid. Sulfuric acid (6M) was added to keep the mixture at pH 1 during the oxalic acid addition. The solution was concentrated on a Rotovap, yielding a white slurry. Hydrochloric acid (6M) was added until the total volume was approximately 300 ml and all the solid had dissolved. The solution was stirred for 30 min at room temperature giving a fine white precipitate. The slurry was extracted with ether [3×400 ml]. A white inorganic salt came out in the aqueous layer. The ether was taken off on a Rotovap. The resulting oil was azeotropically dried using dry benzene on the Rotovap. A white powder (20 g) was isolated. The powder was recrystallized in ethyl acetate-carbon tetrachloride to give 19.5 g of 3,5,6-trichlorotrimellitic acid (II). mp 238°–240°.

C. In a 250 ml R.B. flask was dissolved the trichlorotriacid (II, 10 g) in 30 ml acetic anhydride and the mixture heated at 140°–45° under $N_2$ for 45 min. After cooling, the acetic anhydride was removed on a Rotovap under high vacuum, while heating at 35°–40°. After complete removal of acetic anhydride, the flask was left on high vacuum directly overnight to remove the last traces of acetic anhydride, and the product (III) was used directly.

D. The trichloroanhydride (III, 9.5 g) was mixed with powdered 4-methylresorcinol (8.5 g, dried overnight on high vacuum) in a wide mouth tube and heated in a preheated oil bath at 185°–90°. Anhydrous $ZnCl_2$ (1 g) was added to the mixture and the heating continued for 1.5 hrs with occasional mixing with a spatula, a hard red mass being obtained. The contents were cooled and the red solid scraped off of the tube.

The solid was dissolved with stirring in 300 ml of 8% aq. NaOH, cooled in an ice bath and acidified with 1:1 HCl to pH1. A yellow solid separated out. After filtering and washing with water (150 ml), the precipitate was dried under high vacuum overnight. The dry yellow solid weighed about 15.5 g.

The dried yellow powder was stirred with 200 ml of ethyl acetate overnight, the mixture filtered and the solids washed with 15 ml ethyl acetate. The ethyl acetate filtrate was concentrated on a Rotovap at ~35°–40° to almost dryness. The residue was stirred with 200 ml benzene for 2 hrs and filtered. The filtered solid was stirred with 200 ml of $CH_2Cl_2$ for 3–4 hrs and again filtered. The remaining solid weighed 9.0 g. Its TLC in THF:$CH_2Cl_2$ (1:1) indicated that it is almost pure with one major spot on TLC and a couple of minor spots moving almost with the solvent front. The yellow solid was used without further purification for the next reaction.

The above yellow solid mixture (6.0 g) was dissolved in 150 ml of freshly distilled THF (distilled over $CaH_2$) and 3.0 g DCC added. The clear solution was then stirred overnight. Next day, the white solid which had formed was filtered, the solid washed with 15 ml dry THF and the combined filtrates concentrated to dryness on a Rotovap at ambient temperature. To the solid was then added 200 ml n-hexane and the mixture stirred for 2 hrs to remove excess DCC. The yellow solid was filtered and washed with 50 ml n-hexane. The remaining solid is a mixture of unreacted VI and anhydride VII as shown by TLC (solvent system THF:$CH_2Cl_2$ 60:40). (VI-2,7-dimethyl-9-(2',4'-dicarboxy-3',5',6'-trichlorophenyl)-6-hydroxy-3H-xanthen-3-one; VII-2,7-dimethyl-9-(3',4'-dicarboxy anhydride-2',5',6'-trichlorophenyl)-6-hydroxy-3H-xanthen-3-one).

Example II

Preparation of 2,7-dimethyl-9-(3' or 4'-carboxamido-4' or 3'-carboxy-2',5',6'-trichlorophenyl)-6-hydroxy-3H-xanthen-3-one acetic acid The yellow solid obtained in Example I was dissolved in dry THF (300 ml) and combined with 8.5 g of 3-β-cholestanyl glycinate and the mixture stirred overnight at room temperature. The solvent was then removed and the residual solid stirred with water (150 ml) for 2 hrs. The resulting mixture was acidified with dil HCl to pH1 and stirring continued for 1 hr more in the cold room. The resulting yellow solid was filtered and washed with 100 ml of ice-cold water and dried in vacuo. Its TLC (THF:$CH_2Cl_2$ 1:1) indicated it to be a mixture of only two major compounds. The yellow solid was absorbed on silica gel (30 g) with THF and dried. The dry powder was poured over a dry column of silica gel (200 g) and eluted with THF:$CH_2Cl_2$ mixture (1:4) with the elution followed by TLC. The faster moving spot eluant was collected and the solvent removed to give the cholestanyl ester derivative of the above indicated compound as a yellow powder (2.6 g).

Hydrolysis of the above ester was carried out by dissolving 1.5 g of the ester in 10 ml of THF, adding aq. NaOH (1 g in 70 ml $H_2O$) and stirring the solution for 24 hrs at room temperature. A white solid separated out. The alkaline solution was extracted with ether (3×50 ml) and the aq. solution acidified with conc. HCl to pH 2. A yellow solid separated out. This solution was extracted with ether (3×100 ml), the ethereal solution washed with brine solution (2×15 ml) and upon removal of the ether a yellow solid was obtained, which was dried in vacuo for 4 hrs. The residual mass was stirred with $CH_2Cl_2$ (45 ml) overnight, resulting in a yellow powder precipitating. This was filtered and washed with more CH$_2$Cl$_2$ (20 ml) and the final yellow solid (700 mg) dried in vacuo.

EXAMPLE III

Conjugation of the product of Ex. II to human IgG (a) Preparation of the activated NHS derivative of the dye The product of Ex. II (60 mg) was dissolved in dry THF (1 ml) and NHS (30 mg) added, followed by the addition of DCC (30 mg) and stirring at room temperature for 3 hrs. A white solid separated out which was filtered off. The filtrate was concentrated in vacuo and the residue stirred for 30 min with 10 ml of n-hexane to remove excess DCC. The yellow powder was filtered off. It was used directly.

(b) Reaction of NHS ester of the dye to human IgG

Human IgG (10 mg) was dissolved in 1.2 ml of 0.05M PO$_4$$^{3-}$ buffer at pH 8.0 and cooled to 0°-5° in an ice cold bath. A solution of 1.2 mg of the above prepared NHS ester in dry DMF (40 μl) was added during 20 min to the rapidly stirring protein solution (The pH of the solution is maintained at 8.0 during addition of NHS ester by adding a trace of solid Na$_2$CO$_3$.) After the addition is complete, the mixture is stirred for 1.5 hrs at room temperature and then 1 ml of 2N NH$_2$OH (adjusted to pH 8.1) added and the mixture stirred for 1 hr. more in the cold room. After centrifugation of the reaction mixture, the supernatant solution was purified through Sephadex G-25 column using 0.05M PO$_4$$^{3-}$ buffer at pH 8.0. The faster moving conjugate was found to have $\lambda_{max}^{abs}$ 521-22 nm and $\lambda_{max}^{emission}$ 537-38 nm. This particular conjugate was found to have dye/protein ratio of 7.56 based on uv calculations.

EXAMPLE IV

Conjugate of the product of Ex. II with triiodothyronine (T$_3$) and dextran

In general, great care was taken to avoid the exposure to light of compounds at all stages of the sequence.

A. T$_3$ (1 g) was suspended in dry methyl alcohol (15 ml) and a slow stream of hydrogen chloride gas passed through the suspension for 20 min. A clear solution was obtained. The solvent was removed on a Rotovap at room temperature, and the residual white solid dried in vacuo and used directly.

B. To a mixture of the above ester (70 mg) in dry DMF (1 ml) containing triethylamine (100 μl) was added the NHS ester of the product of Ex. II (prepared from 70 mg in accordance with the procedure described above) and the solution stirred overnight. The DMF was removed in vacuo and the residue treated with dil.HCl resulting in a yellow solid which was filtered, washed with water, and dried in vacuo. Its TLC (THF:CH$_2$Cl$_2$::40:60) indicated that it has one major spot. The material was purified by preparative TLC using 16 plates (20×20 cm) and the above solvent system. The major spot was eluted with methanol and the methanol removed to yield ~40 mg.

C. A solution of the above product (30 mg) in 1N NaOH (2 ml) was stirred at room temperature for 2 hrs. The solution was acidified with dil.HCl and the yellow solid filtered and dried. The acid was further purified by preparative TLC (CH$_2$Cl$_2$:MeOH:AcOH::75:25:1) and the product eluted from silica gel with methanol. After removing the methanol, the residue was dissolved in 1N NaOH, the solution filtered and acidified with dil.HCl. The resulting yellow precipitate was filtered, washed with water and dried overnight in vacuo at 65° to give the desired acid product (13 mg). Its UV spectrum in 0.05M PO$_4$$^{3-}$ buffer had $\lambda_{max}^{absorption}$ 519 nm, and $\lambda_{max}^{emission}$ 533-34 nm.

D. Aminodextran was prepared from BHP activated Dextran 70 (Sigma) as described in copending application Ser. No. 017,874, filed Mar. 3, 1979. BHP activated Dextran 70 (500 mg) was stirred overnight with 10 ml of buffer (0.15M NH$_4$OH and 0.1M NaHCO$_3$-Na$_2$CO$_3$, pH 9.0) at room temperature. β-Mercaptoethanol (70 μl) was added and stirring continued at room temperature for 10 hrs. After dialyzing against water at room temperature over the weekend, the total volume after dialysis was about 14 ml (contains about 500 mg of Dextran 70).

E. A solution of 10 mg of the acid of C in dry THF (1 ml), containing DCC (9 mg) and NHS (5 mg), was stirred overnight. A white solid separated out. After filtering, the filtrate was concentrated in vacuo. The residue was macerated with hexane (10 ml) and the yellow solid (~20 mg) separated. On TLC examination in THF:CH$_2$Cl$_2$ (1:1), the yellow solid appeared to be mostly the NHS ester (higher Rf) with a small amount of starting material (lower Rf).

F. Aminodextran solution (300 μl) prepared above was diluted with 300 μl of 0.1N NaHCO$_3$-Na$_2$CO$_3$ solution (pH 9.0), and to this was added a solution of 0.5 mg of the NHS ester prepared in E in 25 μl of THF. The solution was stirred at room temperature for 1.5 hrs. To this solution was then added 0.3 ml of 3N NH$_2$OH solution (pH 8.0) and the mixture stirred for 45 min at room temperature. After centrifugation for 2 min, the supernatant was purified over G-25 Sephadex column (1×30 cm) using 0.1N NaHCO$_3$-Na$_2$CO$_3$ buffer (pH 9.0). The faster moving conjugate was collected (total volume of conjugate after chromatographing is about 2 ml). It had $\lambda_{max}^{absorption}$ 521-22 nm, $\lambda_{max}^{emission}$ 537-38 nm. Its quantum yield was 43% as compared to the parent fluorescein derivative of Ex. II (based on emission peak area when both are excited at 500 nm).

EXAMPLE V

Preparation of 2,7-dimethyl-9-(2',4' or 5' dicarboxyphenyl)-6-hydroxy-3H-xanthen-3-one and the 4,5-dichloro derivative A. In a reaction flask was combined 1.35 g 4-methylresorcinol, 1 g trimellitic anhydride and 100 mg ZnCl$_2$ and the mixture heated at 195°-200° for 15 min. The resulting solid was macerated with water and filtered. The precipitate was dissolved in 5% NaOH, stirred for 5 min, filtered and the filtrate acidified with dil.HCl to pH2. The resulting solid was recrystallized from methanol to yield an orange red solid. mp>280°.

B. A portion of the above product was dissolved in DMF, and 2.2 equiv. of chlorine in glac. acetic acid added. When no further reaction appeared to be occurring, the product was isolated and purified by preparative TLC using CHCl$_3$:MeOH(80:20).

EXAMPLE VI

Preparation of 2,7-di(2'''-carboxyethyl)-9-(2'-carboxyphenyl)-6-hydroxy-3H-xanthen-3-one Into a reaction flask was introduced 1.1 g of 4-(2'-carboxyethyl)resorcinol, 0.45 g phthalic anhydride and 250 mg ZnCl$_2$ and the mixture heated at 160°-70° for 0.5 hr. After treating with water, and filtering, the solid was dissolved in 5% NaOH, the solution stirred for 15 min, the filtrate acidified with dil HCl to pH2 and the resulting yellow solid filtered and dried. The product was macerated with ethyl acetate and further purified by preparative TLC (CHCl$_3$:MeOH:CH$_3$CO$_2$H glac.::80:20:0.5).

EXAMPLE VII

Preparation of 2,7-di(3''-carboxypropyl)-9-(2',4'-and 3',4'-diicarboxy-3',5',6' and 2',5',6'-trichlorophenyl)-6-hydroxy-3H-xanthen-3-one Following the prior procedures, into a reaction flask was introduced 2.6 g 4-(3'-carboxypropyl)resorcinol, 1.95 g 3,5,6-trichloro-1,2,4-benzenetricarboxylic acid and 100 mg ZnCl$_2$ and the mixture heated at 180°-85° for 40 min. The mixture was worked up as previously described and the product purified by preparative TLC using CHCl$_3$:MeOH:HOAc::80:20:1.

The following table reports the spectroscopic properties of the described compounds.

TABLE III

| Ex. | absorption[1] $\lambda_{max}$ | emission[1] $\lambda_{max}$ | $\epsilon \times 10^3$[1] | $\phi^2$, % |
|---|---|---|---|---|
| I | 516 | 531 | 70.5 | 76 |
| II | 518 | 532-3 | 72.0 | 70 |
| V A | 500 | 518-9 | 67.3 | 92 |
| B | 511-2 | 523-5 |  | 100 |
| VI | 500-1 | 521-2 | 70.0 | 88 |
| VII | 519 | 535 | 69.0 | 64 |

[1]In 0.05 M PO$_4^{3-}$ buffer, pH 8.0
[2]Compared to fluorescein on the basis of emission peak measured in 0.05 M PO$_4^{3-}$ excited at 475 nm.

It is evident from the previous examples that the subject compounds have many desirable properties. The compounds absorb at wavelengths at or in excess of 500, having large Stokes shifts, and their spectroscopic properties are not adversely affected by being conjugated to proteins.

In order to demonstrate further the utility of the subject inventions, immunoassays were carried out, where the fluorescent compound was a compound within the scope of the subject invention. The assay was concerned with immunoglobulin G. The following solutions were employed in preparing reagents for carrying out the assay:

Buffer 0.01M Na$_2$HPO$_4$, 0.15M NaCl, 2%PEG6000, 0.05% NaN$_3$, pH8.0.

Reagent B diluent: 0.05M trizma base, 0.02M glycine, 0.01M benzamine-HCl, 0.15M NaCl, 0.05% NaN$_3$, pH8.0.

Reagent A diluent: 0.05M trizma base, 1% cholate, 0.01M benzamidine-HCl, 0.05% NaN$_3$, pH8.0.

Calibrator diluent: 0.01M Na$_2$ HPO$_4$, 0.15M NaCl, 0.01M benzamidine-HCl, 0.01% NaN$_3$, pH7.2.

Reagent A is a rhodamine-anti(hIgG) conjugate diluted 1:30 with reagent A diluent and having a rhodamine/protein ratio of 11. Reagent B is a 2,7-dimethyl-9-(2',5',6'-trichloro-3' or 4'-carboxamido glycine-4'- or 3'-carboxy)-6-hydroxy-3H-xanthen-3-one conjugate to hIgG diluted 1:26.7 with reagent B diluent and having a fluorescer/protein ratio of about 2.

The calibrators are derived from Freon-dextran sulfate treated serum, diluted with calibrator diluent, except for the 24 mg/ml calibrator which employes undiluted serum. The negative calibrator is assay buffer.

The assay is performed with a Varian Fluorichrom fluorometer (modified), at 25°, employing as the gain a fluorescence signal set to 1600 using a standard solution of $3.8 \times 10^{-9}$M of the fluorescer itself.

The assay is performed by combining 16 μl of the calibrator or sample, diluted with 400 μl of assay buffer, following by the addition of 50 μl each of reagent A and reagent B and an additional 400 μl of assay buffer. After 5 sec, the change in fluorescence is read over a 6 sec period, to determine the rate of change in fluorescence.

A standard curve was prepared having the following higG mg/ml concentrations: 0, 1.6, 5.6, 11.2, 17.6 and 24.0.

A number of samples were then employed and the hIgG determined and compared with commercially available RID or nephenlometric techniques. The following table indicates the results.

TABLE III

| Comparative Method | No. of Samples | Inter-cept | Slope | Correlation Coefficient | Standard Error |
|---|---|---|---|---|---|
| RID | 50 | −0.12 | 1.12 | 0.97 | 1.49 |
| Nephelometry (1) | 25 | 3.87 | 0.72 | 0.91 | 1.76 |
| Nephelometry (2) | 12 | 3.25 | 0.59 | 0.96 | 1.65 |

It is evident from the above results, that there is a consistent relationship between the subject method employing the compounds of the subject invention and other commercially available assays. There is an evident bias in the nephelometric results, possibly due to each of the techniques employing its own method of valuation.

The subject invention provides novel compounds which have important spectroscopic properties, providing for absorption at long wavelengths, high extinction coefficients, sharp absorption bands and fluorescent bands and substantial spacing between absorption and fluorescence bands. These properties are particularly desirable and important to the development of fluorescent techniques or the detection of a wide variety of materials.

Although the foregoing invention has been described in some detail by way of illustration and example for purposes of clarity of understanding, it will be obvious that certain changes and modifications may be practiced within the scope of the appended claims.

What is claimed is:

1. In a method for performing a fluorescent protein binding assay, which comprises combining in an assay medium a sample suspected of containing an analyte and members of a signal producing system wherein one of said members comprises a conjugate of a member of a specific binding pair either ligand or receptor and a spectroscopically active compound, and measuring the level of said signal in said assay medium, the improvement which comprises employing as said conjugate a compound of the formula

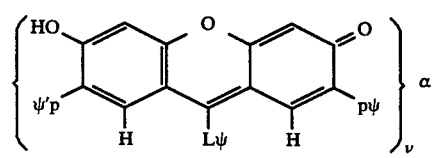

wherein:

α is a member of a specific binding pair either ligand or receptor covalently bonded to one of ψ or ψ';

ρ is an aliphatic hydrocarbon group of from about 1 to 12 carbon atoms.

ψ' is hydrogen or non-oxocarbonyl;

L is a bond or divalent radical;

ψ is a linking group bonded to α or a group terminating in a heteroatom containing functionality when not bonded to α; and ν is a number between 1 and the molecular weight of α divided by 500.

2. In a method for performing a fluorescent protein binding assay, which comprises combining in an assay medium a sample suspected of containing an analyte, and members of a signal producing system wherein one of said members comprises a conjugate of a member of a specific binding pair either ligand or receptor and a spectroscopically active compound, the improvement which comprises employing as said conjugate a compound of the formula

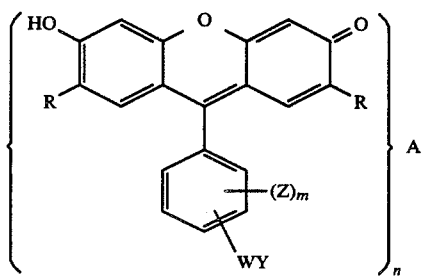

wherein:

R is alkyl or carboxyalkyl of from 1 to 4 carbon atoms:

Z is carboxy;

A is a ligand or receptor;

W is a bond or divalent radical of from 0 to 8 carbon atoms;

Y is methylene or a heteroatom containing linking functionality;

m is 0 to 3;

n is a number between 1 and the molecular weight of A divided by 500; and said portion in the brackets of said formula having from 0 to 6 chloro groups at other than the 1,8-position of the xanthene portion of the molecule.

3. In a method for performing a fluorescent protein binding assay, which comprises combining in an assay medium a sample suspected of containing an analyte, and members of a signal producing system wherein one of said members comprises a conjugate of a member of a specific binding pair either ligand or receptor and a spectroscopically active compound, the improvement which comprises employing as said conjugate a compound of the formula

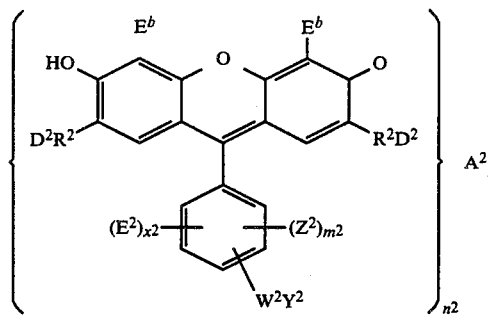

wherein:

$E^b$ is hydrogen or chloro;

$E^2$ is chloro;

$Z^2$ is carboxy;

$R^2$ is alkylene of from 1 to 3 carbon atoms;

$D^2$ is hydrogen or carboxy;

$W^2$ is a bond, alkylene, carboxamidoalkylene, or poly(carboxamidoalkylene), wherein alkylene is of from 1 to 2 carbon atoms;

$Y^2$ is non-oxo-carbonyl, carbamoyl, thiocarbamoyl, amino, methylene, oxy or thio;

$A^2$ is a ligand or receptor;

$m^2$ is 2 to 3;

$X^2$ is 0 to 4; and $n^2$ is a number between 1 and the molecular weight of $A^2$ divided by 500.

4. In a method for performing a fluorescent protein binding assay, which comprises combining in an assay medium a sample suspected of containing an analyte, and members of a signal producing system wherein one of said members comprises a conjugate of a member of a specific binding pair either ligand or receptor and a spectroscopically active compound, which conjugate is further bound to a support, and measuring the level of said signal in said assay medium, the improvement which comprises employing as said conjugate bound to a support a compound of the formula

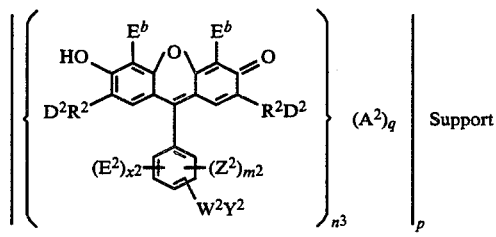

wherein:

$n^3$ is a number between 1 and the molecular weight of $A^2$ divided by 500, with the proviso that when q is 0, $n^3$ is 1;

q is 0 to 1;

p is at least 1 and up to the molecular weight of Support divided by 500;

Support is a molecule of at least about 10,000 molecular weight having a plurality of functionalities for linking;

the group in the brackets is bonded by any convenient functionality by a bond or linking group to the Support;

$E^b$ is hydrogen or chloro;

$E^2$ is chloro;

$Z^2$ is carboxy;

$R^2$ is alkylene of from 1 to 3 carbon atoms;

$D^2$ is hydrogen or carboxy;

$W^2$ is a bond, alkylene, carboxyamidoalkylene or poly(carboxyamidoalkylene), wherein alkylene is of from 1 to 2 carbon atoms;

$Y^2$ is non-oxo-carbonyl, carbamoyl, thiocarbamoyl, amino, methylene, oxy or thio;

$A^2$ is a ligand or receptor bonded to $Y^2$;

$m^2$ is 0 to 3; and $x^2$ is 0 to 4.

5. In a method for performing a fluorescent protein binding assay, which comprises combining in an assay medium a sample suspected of containing an analyte, and members of a signal producing system wherein one of said members comprises a conjugate of a member of a specific binding pair either ligand or receptor and a spectroscopically active compound, the improvement which comprises employing as said conjugate a compound of the formula

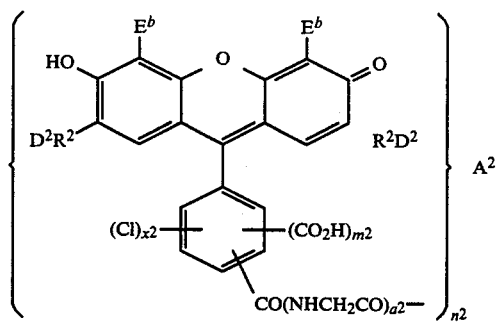

wherein:

$E^b$ is hydrogen or chloro;

$R^2$ is alkylene of from 1 to 2 carbon atoms;

$D^2$ is hydrogen or carboxy;

$m^2$ is 1 to 3;

$x^2$ is 1 to 3;

$a^2$ is 0 to 1;

$A^2$ is a ligand or a receptor, said ligand and receptor being linked by amide linkages;

$n^2$ is 1 when $A^2$ is hydroxyl or an electrophilic ester activating group and is otherwise a number between 1 and the molecular weight of $A^2$ divided by 500.

* * * * *